(12) United States Patent
Ruppersberg

(10) Patent No.: US 10,888,391 B2
(45) Date of Patent: Jan. 12, 2021

(54) OPTICAL FORCE SENSING ASSEMBLY FOR AN ELONGATED MEDICAL DEVICE

(71) Applicant: Ablacon Inc., Wheat Ridge, CO (US)

(72) Inventor: Peter Ruppersberg, Blonay (CH)

(73) Assignee: Ablacon Inc, Wheat Ridge, CO (US)

(*) Notice: Subject to any disclaimer, the term of this patent is extended or adjusted under 35 U.S.C. 154(b) by 280 days.

(21) Appl. No.: 15/577,924

(22) PCT Filed: May 29, 2015

(86) PCT No.: PCT/EP2015/001097
§ 371 (c)(1),
(2) Date: Nov. 29, 2017

(87) PCT Pub. No.: WO2016/192741
PCT Pub. Date: Dec. 8, 2016

(65) Prior Publication Data
US 2018/0161119 A1 Jun. 14, 2018

(51) Int. Cl.
*A61B 90/00* (2016.01)
*A61B 18/14* (2006.01)
(Continued)

(52) U.S. Cl.
CPC ............ *A61B 90/06* (2016.02); *A61B 5/6851* (2013.01); *A61B 5/6852* (2013.01);
(Continued)

(58) Field of Classification Search
CPC .............. A61B 90/06; A61B 2090/064; A61B 2090/065; A61B 5/6851; A61B 5/684;
(Continued)

(56) References Cited

U.S. PATENT DOCUMENTS 8,048,063 B2  11/2011 Aeby et al.
8,852,130 B2  10/2014 Govari
(Continued)

FOREIGN PATENT DOCUMENTS

EP  2 586 363  5/2013

OTHER PUBLICATIONS

ISR for PCT/EP2015/001097, dated Mar. 16, 2017, Ruppersberg.
(Continued)

*Primary Examiner* — Matthew Kremer
*Assistant Examiner* — Avery M Foley
(74) *Attorney, Agent, or Firm* — Woods Patent Law, P.C.

(57) ABSTRACT

The present invention concerns an elongated medical device (1) suitable for intravascular insertion. Said device comprising a flexible elongated body (2) having a distal portion (3) with a distal end (4) and a proximal portion (5) and an optic force sensing assembly (20) disposed within said flexible elongated body (2) proximate said distal end. The optical force sensing assembly (20) comprises a light source (30), which defines a linear optical light source axis (A), and an optical sensor (40), which faces the light source (30) and which defines a linear optical sensor axis (B) and whereat the optical sensor (40) is arranged in a distance ($d_0$, $d_1$) to the light source along the optical sensor axis (B), a mounting assembly (50) for the optical sensor (40) and the light source (30) which allows for relative movement of the light source (30) against the optical sensor (40) at least in the directions X, Y, Z of the Cartesian coordinate system, wherein direction Z is parallel to the direction of the optical sensor axis (B) at least in an initial state of the optical force sensing assembly (20) and whereby X and Y directions are perpendicular to each other as well as perpendicular to Z direction.

17 Claims, 10 Drawing Sheets

(51) Int. Cl.
*G01L 5/166* (2020.01)
*A61B 5/00* (2006.01)
*A61B 17/00* (2006.01)
*A61B 18/00* (2006.01)

(52) U.S. Cl.
CPC ........ *A61B 5/6885* (2013.01); *A61B 18/1492* (2013.01); *G01L 5/166* (2013.01); *A61B 2017/00057* (2013.01); *A61B 2018/00577* (2013.01); *A61B 2090/064* (2016.02)

(58) Field of Classification Search
CPC ... A61B 5/6843; A61B 5/6844; A61B 5/6846; A61B 5/6847; A61B 5/6852; A61B 5/6885; A61B 5/6886; A61B 18/1492; A61B 2017/00057; A61B 2018/00577; G01L 5/166
See application file for complete search history.

(56) References Cited

U.S. PATENT DOCUMENTS

| | | | |
|---|---|---|---|
| 2008/0051704 A1 | 2/2008 | Patel | |
| 2008/0245955 A1* | 10/2008 | Tachi | G01L 1/247 250/221 |
| 2008/0275367 A1 | 11/2008 | Barbagki et al. | |
| 2009/0177095 A1* | 7/2009 | Aeby | A61B 5/0084 600/478 |
| 2011/0270046 A1* | 11/2011 | Paul | A61B 5/065 600/300 |
| 2013/0204142 A1* | 8/2013 | Bertholds | G01L 5/166 600/478 |
| 2013/0220032 A1* | 8/2013 | Packirisamy | G01B 11/18 73/862.624 |
| 2014/0209797 A1 | 7/2014 | Klimovitch | |
| 2014/0364848 A1* | 12/2014 | Heimbecher | A61B 5/6885 606/41 |
| 2015/0350502 A1* | 12/2015 | Lin | H04N 5/2254 348/65 |

OTHER PUBLICATIONS

WO for PCT/EP2015/001097, dated Mar. 16, 2017, Ruppersberg.
IPR for PCT/EP2015/001097, dated Sep. 6, 2017, Ruppersberg.
ISR for PCT/EP2015/000870, dated Nov. 2015, Ruppersberg.
WO for PCT/EP2015/000870, dated Apr. 2015, Ruppersberg.

* cited by examiner

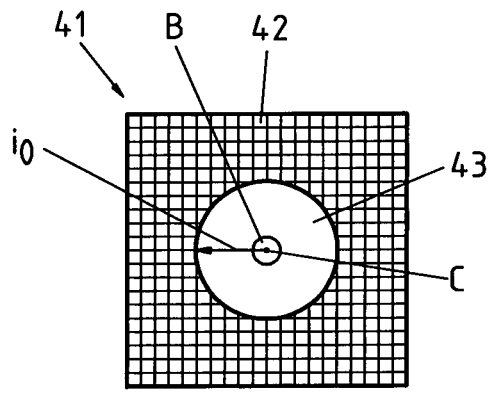
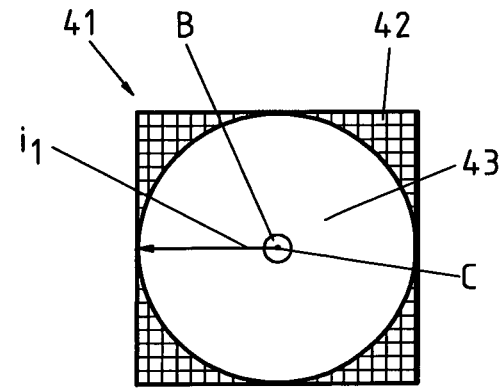
FIG.7  FIG.8
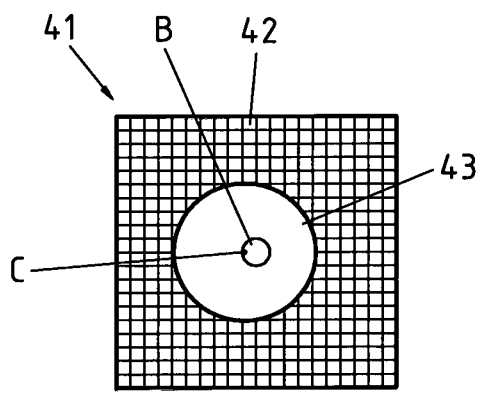
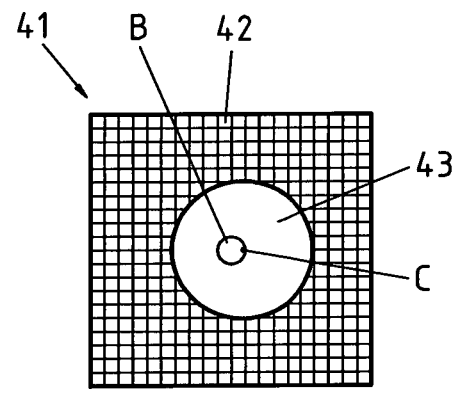
FIG.9  FIG.10
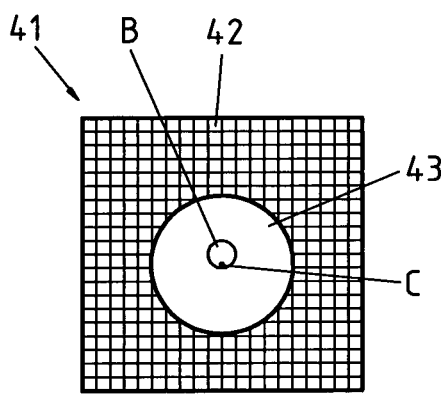
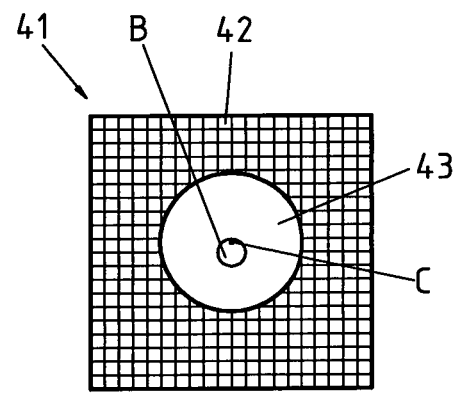
FIG.11  FIG.12

OPTICAL FORCE SENSING ASSEMBLY FOR AN ELONGATED MEDICAL DEVICE

RELATED APPLICATION

This application is a national stage entry of, and claims priority and other benefits from: (a) International Patent Application PCT/EP2015/001097 to Ruppersberg filed on May 29, 2015, entitled "Elongated Medical Device Suitable for Intravascular Insertion, Optical Force Sensing Assembly for an Elongated Medical Device and Method of Making a Medical Optical Force Sensing Assembly" (hereafter "the '001097 patent application"), and (b) International Patent Application PCT/EP2016/000870 to Ruppersberg filed on May 25, 2016, entitled "Elongated Medical Device Suitable for Intravascular Insertion, Optical Force Sensing Assembly for an Elongated Medical Device and Method of Making a Medical Optical Force Sensing Assembly" (hereafter "the '000870 patent application"). The respective entireties of the '001097 and '000870 patent applications are hereby incorporated by reference herein.

FIELD OF THE INVENTION

The present invention relates generally to elongated medical devices suitable for intravascular insertion, comprising a flexible elongated body having a distal portion with a distal end and a proximal portion and an optic force sensing assembly disposed within said flexible elongated body proximate said distal end, such as manually or robotically steerable catheters for the exploration or treatment of vessels or organs or other body cavities or guide wires for guiding catheters or the like medical apparatuses.

The invention relates to a medical optical force sensing assembly. Further, the present invention relates to a method of making a medical optical force sensing assembly. The present invention especially relates to an elongated medical device suitable for intravascular insertion with individual features of claim 1, a medical optical force sensing assembly with individual features of the respective independent claim, as well as a method of making a medical optical force sensing assembly with individual features of the respective independent method claim.

BACKGROUND

Elongated medical devices suitable for intravascular insertion, such as catheters, especially ablation catheters, and guide wires for guiding catheters through vessels, organs or other body cavities are e.g. used in the treatment of atrial fibrillation (Afib). Atrial fibrillation is the most frequent arrhythmic disorder of the heart. Blood clotting occurring in the fibrillating atria is one main cause of stroke. In so far, Afib is one of the most important disorders associated with a high fatal risk. The cause for Afib has been subject to intensive scientific investigations and is meanwhile largely understood. In most patients, the pulmonary veins draining into the left atrium are the sources of rapid arrhythmic action potentials which trigger circular excitation patterns (rotors), in the left atrium that induce a high frequency fibrillation through their re-entry mechanism. Those rotors have the character of small action potential cyclones of 2 to 3 $cm^2$ in size. The likelihood of occurrence of those rotors and the frequency of pathological action potential generation in the pulmonary veins increases with fibrotic structural changes and certain modifications of ion channel expression patterns in atrial cells with age.

The only potentially curative treatments for Afib are open heart surgery or catheter ablation of those parts of the atrial wall tissue which originate, transmit or maintain the pathologic excitation circles.

Today the use of catheter ablation like open heart surgery is still limited by the potentially fatal risk of some severe side effects associated with the procedure: When the integrity of the atrial wall is destroyed by too intense ablation, perforations of the atrial wall into the pericardium or fistulas into the esophagus can have severe to deadly outcomes. The alteration of the endocardial cells on a larger surface can initiate clotting in the treated atrium which may lead to deadly strokes. That is why the procedure requires full anticoagulation. Last but not least, if the intensity of the ablation is kept too low to avoid those side effects in many cases the therapeutic effect is insufficient and patients face a success rate of the treatment of only 50-70% on average.

To improve the situation, force sensing catheters are used that allow to better control the catheter positioning pressure which has an influence on the intensity of ablation. Further, water irrigation tries to keep the endothelial tissue free of lesions and micro-calorimetric sensors try to measure and control the heat in the tissue.

SUMMARY

U.S. Pat. No. 8,048,863 B2 discloses a catheter for diagnosis or treatment of a vessel or organ in which a flexible elongated body includes a triaxial force sensor formed of a housing and a plurality of optical fibres associated with the housing that measure changes in the intensity of light reflected from the lateral surfaces of the housing resulting from deformation caused by forces applied to a distal extremity of the housing. A controller receives an output of the optical fibres and computes a multi-dimensional force vector corresponding to the contact force. The disadvantage of this type of catheter including a triaxial force sensor is the high production costs of the sensor.

U.S. Pat. No. 8,852,130 B2 discloses a medical probe, including a flexible insertion tube, having a distal end for insertion into a body cavity of a patient and which is configured to be brought into contact with tissue in the body cavity. The probe further includes a sensor tube of an elastic material, contained inside the distal end of the insertion tube and configured to deform in response to forces exerted by the tissue on the distal end. The probe also includes a plurality of strain gauges fixedly attached to a surface of the sensor tube at different, respective locations and configured to generate respective signals in response to deformations of the sensor tube.

US 2008/0275367 A1 discloses robotic instrument systems and methods for generating a geometric map of an area of body tissue which is correlated with a tissue characteristic such as tissue compliance or related property. The system comprises a robotically controlled catheter which is controlled by a robotic instrument driver. A force sensor system is provided that generates force signals responsive to a force applied to the distal end of the catheter. A position determination system is also provided which generates position signals responsive to the location of the distal end of the catheter. A computer is configured to receive and process the force signals and position signals to generate a geometric map of an area of body tissue correlated to the tissue compliance of different regions of the body tissue or a tissue characteristic determinable from the tissue compliance.

The force sensor mechanism of US 2008/0275367 A1 is complex as it needs a ditherer to be functionable. This makes the system costly and fault-prone.

It is hence an object of the present invention to provide an elongated medical device suitable for intravascular insertion that avoids the disadvantages of the prior art, which is fail-safe and inexpensive to produce.

It is another object of this invention to provide a medical optical force sensing assembly that permits a 3D sensing of forces applied to the sensor. It is a further object of the present invention to provide a method of making a medical optical force sensing assembly that allows for 3D sensing of forces applied to the force sensing assembly.

These and other objects of the present invention are accomplished by providing an elongated medical device suitable for intravascular insertion that comprises a light source which defines a linear optical light source axis and an optical sensor which faces the light source and which defines a linear optical sensor axis and whereby the optical sensor is arranged in a distance to the light source along the optical sensor axis, a mounting assembly for the optical sensor and the light source which allows for relative movement of the light source against the optical sensor at least in the directions X, Y, Z of a Cartesian coordinate system, whereby direction Z is parallel to the direction of the optical sensor axis at least in an initial state of the optical force sensing assembly and whereby X and Y directions are perpendicular to each other as well as perpendicular to Z direction.

The optic force sensing assembly according to the invention has a fail-safe uncomplicated structure and is low-priced in product.

The optical light source that faces the optical sensor is in operation of the optic force sensing assembly sensed by the optical sensor and any move of the light source relative to the optical sensor is recognized by the optical sensor in that the light of the light source falling on the optical sensor changes in its intensity and the size of the sensor array illuminated by the light.

In an advantageous embodiment of the present invention, the optical sensor and the light source are both disposed at the distal portion of the elongated body. The advantage of this arrangement is that any force applied to the distal end of the distal portion is very directly translated to the optic force sensing assembly which means that any measurement of force is very direct and without any deferment.

Preferably, the distance between the optical sensor and the light source along the optical sensor axis has a maximum length of 10 mm, which allows for a very compact design of the optic sensor part of the optic force sensing assembly. More preferably, the distance between the light source and the optical sensor is 1 mm, even more preferably 0.5 mm.

In a further favorable embodiment of the invention, the optical sensor is designed as a camera module, preferably as a wafer-level camera. Such a camera module, especially the wafer-level camera allows for a high resolution of the optical force sensing assembly in the range of 0.01 N+/−0.005 N and a sampling rate of ≥25 samplings per second. This sampling rate is identical with the video rate of the wafer-level camera. Further, such camera modules, like wafer-level cameras, are available in very small sizes, smaller than a match head. An alternative optical sensor may comprise a combination of a cmos sensor and an aperture, or an array of photo-diodes which may be combined with a lens or an aperture.

In a further favorable embodiment of the invention, the camera module, especially the wafer-level camera, is smaller than 1.5 mm by 1.5 mm in its width and/or smaller than 1.5 mm in its diameter, whereat each of width and diameter is in a direction perpendicular to the optical sensor axis. A camera size of this range allows for an integration of this optical force sensing assembly even in an elongated medical device such as a guide wire for the use in even very small vessels or other body cavities. A preferred size of the camera module is 1 mm by 1 mm in its width and/or 1 mm in its diameter, whereat each of width and diameter is in a direction perpendicular to the optical sensor axis. The length of the camera module along the optical sensor axis may be 2.5 mm or smaller, preferably 2 mm or smaller and even more preferably 1.7 mm.

In a further preferred embodiment the camera module, like the wafer-level camera, has a view angle in air between 60 and 180 degrees, more preferably between 90 and 120 degrees. These view angles are supportive to the high resolution of the optical sensor part of the optical force sensing assembly of 0.01 N+/−0.005 N.

In a further preferred embodiment of the invention the light source is formed as a point light source that preferentially comprises an LED. The LED has the advantage that very small sized LED's are available. So, the LED may be smaller than 1 mm, especially smaller than 0.5 mm, preferably between 0.05 mm to 0.4 mm, in respect of its width or diameter. The advantages of such a point light source are homogenous light, low power consumption and their small size.

In a further advantageous embodiment of the invention, the light source optically cooperates with a diffusor. The diffusor may be arranged adjacent to the light source, especially directly adjacent to the light source and accounts for the light source generating a very diffuse and uniformly distributed light cone that is directed towards the optical sensor. The diffusor is preferably arranged in a way that its optical axis runs coaxially with the optical light source axis.

In an alternative advantageous embodiment of the invention, the light source optically cooperates with a light guide. This light guide may run coaxially with the optical light source axis The advantage is that the light guide allows a larger distance between light source and optical sensor/camera module.

In a further preferred embodiment of the invention, the light guide is formed as a light guiding fibre e.g. made of glass, especially optical glass, or of a plastic material, like polymethylmethacrylate (PMMA).

In a further preferred embodiment of the present invention, the mounting assembly comprises a light source mounting that mounts the light source and an optical sensor mounting that mounts the optical sensor and an elastic element, especially a spring element, which movably connects the light source mounting and the optical sensor mounting. The wording "movably connecting the light source mounting and the optical sensor mounting" does not necessarily mean that the light source mounting and the optical sensor mounting are fixedly connected by the elastic element to each other. The elastic element posed between the light source mounting and the optical sensor mounting allows for an elastic movability of the light source and the optical sensor relative to each other in the three directions X, Y, Z of the Cartesian coordinate system, thus allowing the optical force sensing assembly to react even on smallest forces applied upon it. Also the elastic element, especially the spring element, biases the light source in an axial direction away from the optical sensor.

In a further favorable embodiment, the elastic element is formed as a helical spring. This spring may include a metal core (e.g. spring steel, stainless steel, titanium, nitinol or Platinum Iridium) which may be hollow or massive and which may be surrounded by a plastic material cover. The plastic material may be a biocompatible elastomer like ChronoPrene™ or a silicone rubber elastomer.

The elastic element, which is formed as a helical spring, may cooperate with a flexible tube which may be arranged radially outwardly of the helical spring and which may follow each move of the helical spring (each compression and depression as well as each sideward movement of the spring). By means of the outwardly arranged tube which may be formed as a silicone tube, the elongated medical device may be fluid sealed to the outside, avoiding any liquids to intrude into the elongated medical device in the area of the helical spring and the parts of the optical force sensing assembly.

In an alternative embodiment, the elastic element may be formed as an elastic tube. The elastic tube could be massive or it may have at least one recess, opening, perforation or the like. Advantageously, the elastic tube may be perforated in a regular pattern in order to save material and to reduce weight.

In a further preferred embodiment, the elastic element is made at least partially out of a rubber-like material. This material may be a coating on a metal core or an element like the elastic tube may be formed completely out of this rubber-like material. The rubber-like material may e.g. be ChronoPrene™ or Silicone rubber.

Advantageously, the light source mounting is rigidly connected to the distal end of the elongated body and by doing so it is adapted to follow any move of the distal end relative to the adjacent area of the distal portion. Especially, the light source mounting may be rigidly connected to the distal end of a tip electrode of an elongated medical device, such as a catheter. The connection of the light source mounting to the distal end may be reached by any kind of glueing, welding, brazing/soldering or by means of a mechanical connection including screwing, pressing, including press fit, hammering or the like.

As the light source mounting is fixedly connected to the distal end of the elongated body, it will immediately follow any move of this distal end relative to an adjacent area of the distal portion.

Alternatively, the light source mounting may be fixedly connected to the elastic element, like the helical spring or the elastic tube, and it may be biased towards the distal end of the elongated body to follow any move of the distal end.

In a further advantageous embodiment of the invention, the mounting assembly is adapted to movably connect the light source mounting to the optical sensor mounting in a way that the optical light source axis and the optical sensor axis always run parallel to each other. While the optical force sensing assembly may sense any movement in a direction X, Y, Z, a force applied to the optical force sensing device will be only sensed in Z direction. This force of cause may include force components applied in an angle to the Z direction, but may also include a force vector in Z direction.

In a further advantageous embodiment of the invention, the camera module, like the wafer-level camera, has a pixel array of n pixels, whereat in operation a contiguous array of pixels is receiving light from the light source, whereat the size of the illuminated contiguous pixel array is proportional to a force applied to the distal end in the Z direction. With this embodiment, the force applied to the distal end in the Z direction can be easily measured based on the number of pixels that are illuminated by light received from the light source.

Preferably, the force applied to the distal end in the Z direction may be calculated by the formula $F=k \times d_0 \times (1-i_0/i_1)$. In this formula k is the spring constant in N/mm, $d_0$ is the distance in mm of the optical sensor to the light source in the initial position of the light source in respect to the optical sensor when no force is applied to the distal end of the elongated body, $i_0$ is a measure of the size of the illuminated contiguous pixel array that is receiving light from the light source in the initial position of the light source in respect to the optical sensor when no force is applied to the distal end of the elongated body and $i_1$ is a measure of the size of the illuminated contiguous pixel array that is receiving light from the light source in a position of the light source in respect to the optical sensor when the force is applied to the distal end of the elongated body. Calculation of the force applied to the distal end in Z direction by means of the presented formula could e.g. be performed in a processing and control unit which is connected at least to the optical sensor.

Output of the force data to an operating person of the elongated medical device such as a catheter or a guide wire is important as it makes the application of such medical devices safer. Force data delivered from the optical force sensing assembly allows to better control the positioning pressure with which the distal end of the elongated medical device, such as a catheter or a guide wire, is pressed against the inner wall of a vessel, organ or other body cavity which is to be treated by means of the elongated medical device.

In an advantageous embodiment, the optical force sensing assembly is designed in a way that in operation, a center of the illuminated contiguous pixel array is coaxial with the optical sensor axis when there is no force applied to the distal end in the X or Y directions and that in operation, the center of the illuminated contiguous pixel array is non-coaxial to the optical sensor axis when there is a force applied to the distal end in the X or Y directions or any combination thereof. In this embodiment, any force applied in the X or Y directions can be measured by the form of the illuminated contiguous pixel array which will deviate from the illuminated contiguous array that is present in the initial position of the light source in respect to the optical sensor when there is no force applied to the distal end of the elongated body.

The deviation in shape of the illuminated contiguous pixel array hence is a measure for a force vector applied in the X and/or Y directions or any combination of these.

In a further advantageous embodiment of the invention, the medical device comprises a data processing and control unit that is set up to process force sensing data delivered from the optical sensor via a data line and to output force data by means of a data output unit. Force sensing data may hence be provided to the operating personnel in a convenient way.

Advantageously, the medical device is formed as a catheter for the exploration or treatment of a vessel, organ or other body cavity. This catheter contains one or more of the inventive features described before.

Alternatively, the medical device may be formed as a guide wire for guiding a catheter or the like medical apparatus through a vessel, organ or other body cavity, whereby the guide wire includes one or more of the inventive features described before.

The objects of the present invention are further accomplished by providing a medical optical force sensing assembly comprising a light source, which defines a linear optical light source axis, an optical sensor, which defines a linear optical sensor axis and which faces the light source, the optical sensor being arranged in distance to the light source along/in direction of the optical axis, a mounting assembly for the optical sensor and the light source, which allows for relative movement of the light source against the optical sensor at least in the directions X, Y, Z of a Cartesian coordinate system, whereby direction Z is parallel to the optical sensor axis at least in an initial state of the medical optical force sensing assembly and whereby X and Y directions are perpendicular to each other as well as perpendicular to Z direction.

The optic force sensing assembly according to the invention has a fail-safe incomplicated structure and is low-priced in production. The optical light source that faces the optical sensor is in operation of the optic force sensing assembly sensed by the optical sensor and any move of the light source relative to the optical sensor is recognized by the optical sensor in that the light of the light source falling on the optical sensor may change in its intensity, in the size of the sensor array illuminated by the light and in the angle in which it is falling onto the optical sensor.

In an advantageous embodiment of the medical optical force sensing assembly, the distance between the optical sensor and the light source along the optical sensor axis has a maximum length of 10 mm, which allows for a very compact design of the optic sensor part of the optic force sensing assembly. More preferably, the distance between the light source and the optical sensor is 1 mm, even more preferably 0.5 mm.

Preferably, the optical sensor is designed as a camera module, more preferably as a waver-level camera. Such a camera module, especially the waver-level camera allows for a high resolution of the optical force sensing assembly in the range of 0.01 N+/−0.005 N and a sampling rate of ≥25 samplings per second. This sampling rate is identical with the video rate of the waver-level camera. Further, such camera modules, like waver-level cameras, are available in very small sizes, smaller than a match head. An alternative optical sensor may comprise a combination of a cmos sensor and an aperture, or an array of photo-diodes which may be combined with a lens or an aperture.

In a further favorable embodiment of the medical optical force sensing assembly, the camera module, especially the waver-level camera, is smaller than 1.5 mm by 1.5 mm in its width and/or smaller than 1.5 mm in its diameter, whereat each of width and diameter is in a direction perpendicular to the optical sensor axis. A camera size of this range allows for integration of this optical force sensing assembly even in very thin medical devices such as guide wires or catheters for the use in even very small vessels or other body cavities. A preferred size of the camera module is 1 mm by 1 mm in its width and/or 1 mm in its diameter, whereat each of width and diameter is in a direction perpendicular to the optical sensor axis. The length of the camera module along the optical sensor axis may be 2.5 mm or smaller, preferably 2 mm or smaller and even more preferably 1.7 mm. In a further preferred embodiment of the medical optical force sensing assembly, the camera module, like the waver-level camera, has a view angle in air between 60 and 180 degrees, more preferably between 90 and 120 degrees. These view angles are supportive to the high resolution of the optical sensor part of the optical force sensing assembly of 0.01 N+/−0.005 N.

In a further preferred embodiment of the invention, the light source is formed as a point light source that preferentially comprises an LED. The LED has the advantage that very small sized LED's are available. So, the LED may be smaller than 1 mm, especially smaller than 0.5 mm, preferably between 0.05 mm to 0.4 mm, in respect of its width or diameter. The advantages of such a point light source are their homogenous light, low power consumption and their small size.

In a further advantageous embodiment of the medical optical force sensing assembly, the light source optically cooperates with a diffusor may be arrange adjacent to the light source, especially directly adjacent to the light source and accounts for the light source generating a very diffuse and uniformly distributed light cone that is directed towards the optical sensor. The diffusor is preferably arranged in a way that its optical axis runs coaxially with the optical light source axis. In an alternative advantageous embodiment of the inventive medical optical force sensing assembly, the light source optically cooperates with a light guide. This light guide may run coaxially with the optical light source axis. The advantage is that the light guide allows a larger distance between light source and optical sensor/camera module.

In a further preferred embodiment of the invention, the light guide is formed as a light guiding fiber, e.g. made of glass, especially optical glass, or of a plastic material, like polymethylmethacrylate (PMMA).

In a further preferred embodiment of the inventive medical optical force sensing assembly, the mounting assembling comprises a light source mounting that mounts the light source and an optical sensor mounting that mounts the optical sensor and an elastic element, especially a spring element, which movably connects the light source mounting and the optical source mounting. The wording "movably connecting the light source mounting and the optical sensor mounting" does not necessarily mean that the light source mounting and the optical sensor mounting are fixedly connected by the elastic element to each other. The elastic element arranged between the light source mounting and the optical sensor mounting allows for an elastic movability of the light source and the optical sensor relative to each other in the three directions X, Y, Z of the Cartesian coordinate system, thus allowing the optical force sensing assembly to react even on smallest forces applied upon it. Also the elastic element, especially the spring element, biases the light source in an axial direction away from the optical sensor.

In a further favorable embodiment, the elastic element is formed as a helical spring. This spring may include a metal core (e.g. spring steel, stainless steel, titanium, nitinol or Platinum Iridium) which may be hollow or massive and which may be surrounded by a plastic material cover. The plastic material may be a biocompatible elastomer like ChronoPrene™ or silicone rubber elastomer.

The elastic element, which is formed as a helical spring, may cooperate with a flexible tube which may be arranged radially outwardly of the helical spring and which may follow each move of the helical spring (each compression and depression as well as each sideward movement of the spring). By means of the outwardly arranged tube, which may be formed as a silicone tube, the elongated medical device may be fluid-tight to the outside, avoiding any liquids to intrude into the elongated medical device in the area of the helical spring and the parts of the optical force sensing assembly.

In an alternative embodiment, the elastic element may be formed as an elastic tube. The elastic tube could be massive or may have at least one recess, opening, perforation or the like. Advantageously, the elastic tube may be perforated in a regular pattern in order to save material and to reduce weight.

In a further preferable embodiment, the elastic element is made at least partially out of a rubber-like material. This material may be coating on a metal core or an element like the elastic tube may be formed completely out of this rubber-like material. The rubber-like material may e.g. be ChronePrene™ or silicone rubber.

In a further preferred embodiment of the medical optical force sensing assembly, the light source mounting is rigidly connected to the distal end of the elongated body and by doing so it is adapted to follow any move of the distal end relative to the adjacent area of the distal portion. Especially, the light source mounting may be rigidly connected to the distal end of a tip electrode of the elongated medical device, such as a catheter or a guide wire. The connection of the light source mounting to the distal end may be reached by any kind of glueing, welding, brazing/soldering or by means of a mechanical connection including screwing, pressing, including press fit, hammering or the like.

As the light source mounting is fixedly connectable to the distal end of an elongated body, it may immediately follow any move of the distal end of an elongated body relative to an adjacent area of the distal portion.

Alternatively, the light source mounting may be fixedly connected to the elastic element, like the helical spring or the elastic tube. It may be biased towards the distal end of an elongated body into which it is integrated, to follow any move of this distal end.

In a further advantageous embodiment of the medial optical force sensing assembly, the mounting assembly is adapted to movably connect the light source mounting to the optical sensor mounting in a way that the optical light source axis and the optical sensor axis always run parallel to each other. While the optical force sensing assembly may sense any movement in a direction X, Y, Z. A force applied to the optical force sensing device will only be sensed in Z direction. This force of course may include force components applied in an angle to the Z direction, but may also include a force vector in Z direction.

In a further advantageous embodiment of the medical optical force sensing assembly, the camera module, like the waver-level camera, has a pixel array of n pixels, whereat in operation a contiguous array of pixels is receiving light from the light source, whereat the size of the illuminated contiguous pixel array is proportional to a force applied to one of the light source mounting and the optical source mounting in the Z direction. With this embodiment, the force applied to the medical optical force sensing assembly in the Z direction can easily be measured based on the number of pixels that are illuminated by the light received from the light source.

Preferably, the force applied to the medical optical force sensing assembly in the Z direction, may be calculated by the formula $F=k\times d_0\times(1-i_0/i_1)$. In this formula k is the spring constant in N/mm, $d_0$ is the distance in mm of the optical sensor to the light source in the initial position of the light source in respect to the optical sensor when no force is applied to the distal end of the elongated body, $i_0$ is a measure of the size of the illuminated contiguous pixel array that is receiving light from the light source in the initial position of the light source in respect to the optical sensor when no force is applied to the distal end of the elongated body and $i_1$ is a measure of the size of the illuminated contiguous pixel array that is receiving light from the light source in the position of the light source in respect to the optical sensor when the force is applied to the distal end of the elongated body. Calculation of the force applied to the distal end in Z direction by means of the presented formula e.g. performed in a processing and control unit which is connected at least to the optical sensor.

Output of the force data to an operating person of the elongated medical device such as a catheter or a guide wire is important as it makes the application of such medical devices safer. Force data delivered from the optical force sensing assembly allows to better control the positioning pressure with which the distal end of the elongated medical device, such as a catheter or a guide wire, is pressed against the inner wall of a vessel, organ or other body cavity which is to be treated by means of the elongated medical device.

In a further advantageous embodiment of the medical optical force sensing assembly, the optical force sensing assembly is designed in a way that in operation, a center of the illuminated contiguous pixel array is coaxial with the optical sensor axis when there is no force applied to any one of the light source mounting and the optical sensor mounting in the X or Y directions and that in operation the center of the illuminated contiguous pixel array is non-coaxial to the optical sensor axis when there is a force applied to any one of the light source mounting and the optical sensor mounting in the X or Y directions or any combination thereof. In this embodiment, any force applied in the X or Y directions can be measured in the form of the illuminated contiguous pixel array which will deviate from the illuminated contiguous array that is present in the initial position of the light source in respect to the optical sensor when there is no force applied to any one of the light source mounting and the optical sensor mounting in the X or Y directions. The deviation in shape of the illuminated contiguous pixel array hence is a measure for a force vector applied in the X and/or Y directions or any combination of these.

Preferably, the medical optical force sensing assembly is adapted to be connected to a data processing and control unit that is set up to process force sensing data delivered from the optical sensor via data line into output force data by means of a data output unit. Force sensing data may hence be provided to the operating personal in a convenient way.

A method of making a medical optical force sensing assembly according to the invention comprises: Providing a mounting assembly that comprises a light source mounting for a light source and an optical sensor mounting for an optical sensor, mount the light source on the light source mounting and the optical sensor on the optical sensor mounting so that the light source faces the optical sensor, arrange an elastic element between the light source mounting and the optical sensor mounting to moveably connect the light source mounting and the optical sensor mounting and to allow for a relative movement of the light source against the optical sensor at least in the directions X, Y, Z of a Cartesian coordinate system. This method allows for an easy production of a fail-safe and cost-efficient optical force sensing assembly that allows to sense forces applied to the optical force sensing assembly in the directions X, Y, Z of the Cartesian coordinate system as well as any forces applied to any direction that includes vectors in any one of the X, Y, Z directions.

Advantageously, the method includes that the optical sensor defines a linear optical sensor axis and the optical sensor is arranged in a distance to the light source along its optical sensor axis, whereby direction Z is parallel to the direction of the optical sensor axis at least in an initial state of the medical optical force sensing assembly and whereby X and Y directions are perpendicular to each other as well as perpendicular to the Z direction.

BRIEF DESCRIPTION OF THE DRAWINGS

Further features of the invention, its nature and various advantages will become more apparent from the accompanying drawings and the following detailed description of the preferred embodiments, in which:

FIG. 7 is a top view on the pixel array of the optical sensor in the initial state of the medical device according to FIG. 2;

FIG. 8 is a top view of the pixel array of the optic sensor in another state of the medical device according to FIG. 3, with a force applied in direction Z on the distal end of the distal portion;

FIG. 9 is another top view on the pixel array of the optical sensor in a further state of the medical device;

FIG. 10 is a further top view on the pixel array of the optical sensor in a further state of the medical device with a force applied to another side of the distal portion;

FIG. 11 is a further top view on the pixel array of the optical sensor in a further state of the medical device with a force applied to another side of the distal portion;

FIG. 12 is a further top view on the pixel array of the optical sensor in a further state of the medical device with a force applied to another side of the distal portion according to FIG. 4;

DETAILED DESCRIPTION

Figure 1:
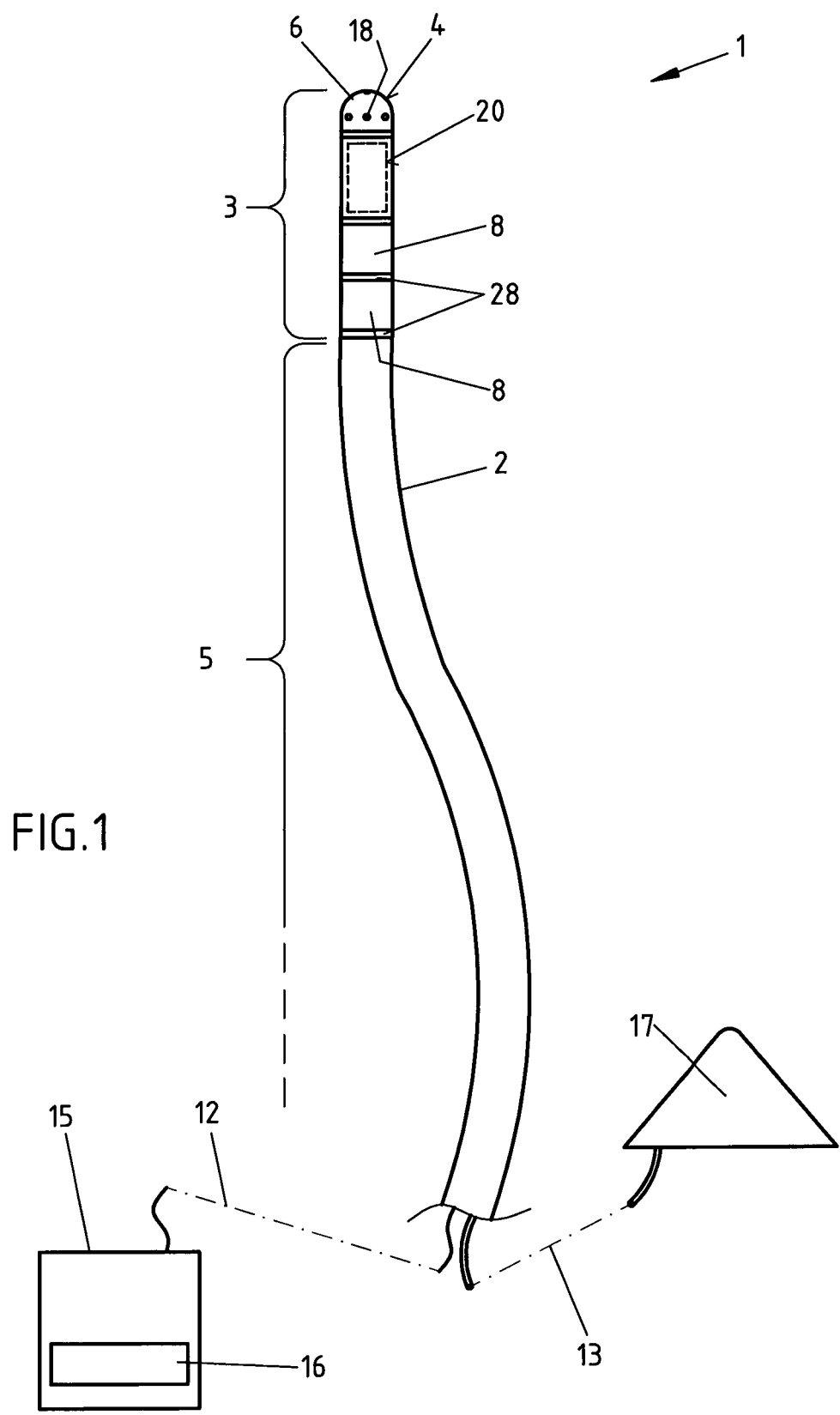
FIG. 1 is a schematic view of an elongated medical device in a first embodiment which is a catheter for exploration or treatment of a vessel or organ or other body cavity.
Figure 2:
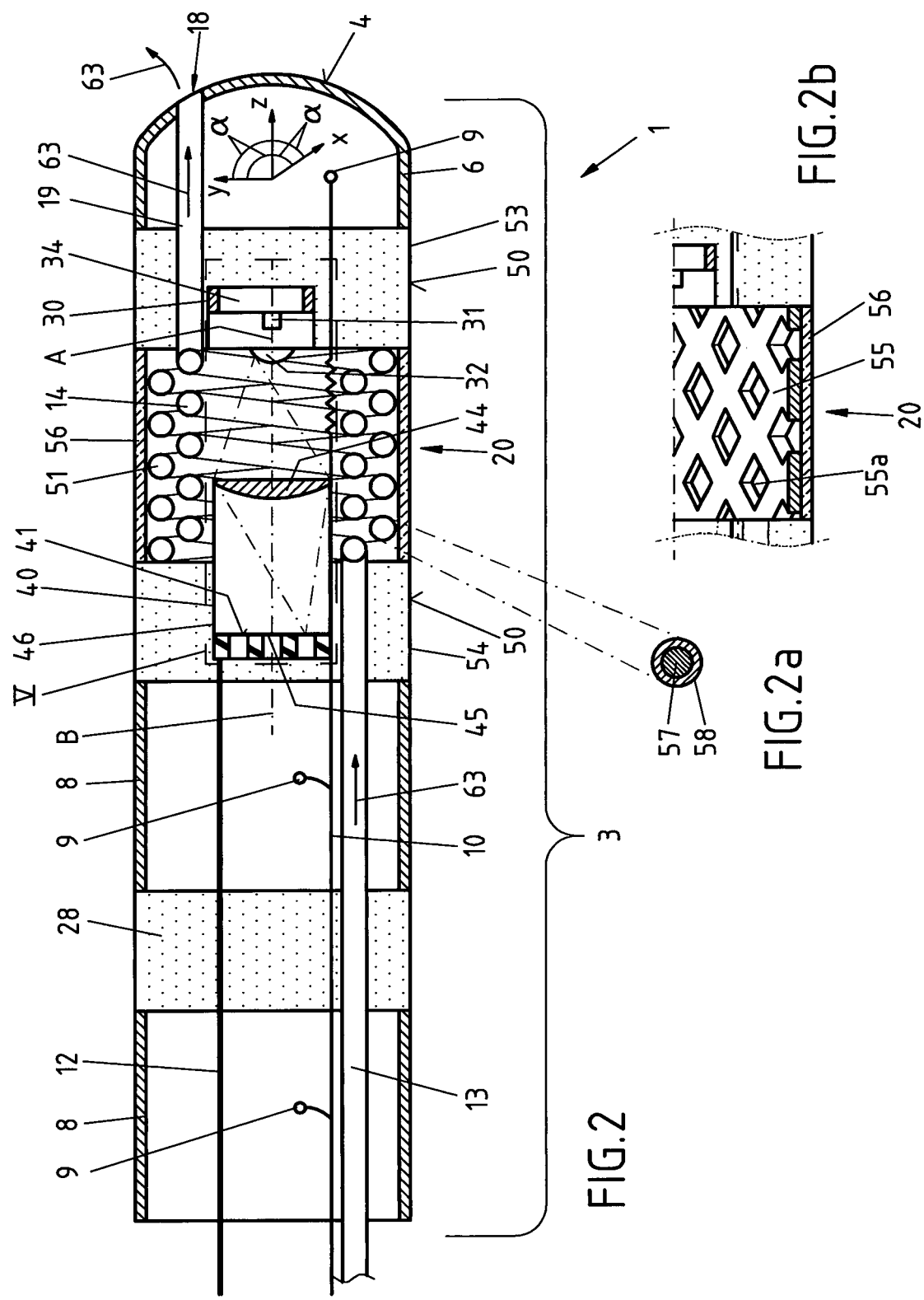
FIG. 2 is a cut view of the distal part of the elongated medical device of FIG. 1 in a first state.

The present invention is directed to an elongated medical device suitable for intravascular insertion, such as a catheter for exploration or treatment of a vessel, organ or other body cavity or a guide wire for guiding a catheter or the like medical apparatus through a vessel, organ or other body cavity. The medical device has an optical force sensing assembly with which contact forces between a distal portion of the medical device and a wall of the vessel, organ or other body cavity can be measured. In operation of the medical device, the force sensing ability may be used periodically to measure the contact forces at certain points, or, alternatively, it may be used to continuously monitor such contact forces to support the operation of the medical device.

Referring to FIG. 1-6, an elongated medical device 1 is formed as an ablation catheter, e.g. to be used in the curative treatment of Artrial fibrillation and other hearth rhythm diseases like Atrial Flutter, Accessory Pathways or Ventricular Tachycardia. The elongated medical device 1 comprises an elongated body 2, which is only partly shown in FIG. 2. At a distal portion 3 of the elongated medical device 1, there is a tip electrode 6 arranged at its distal end 4. Further, two annular electrodes 8 are arranged at the distal portion 3 of the elongated body 2 and are separated to each other by intermediate isolation elements 28. A proximal portion 5 of the elongated body 2 is formed as a flexible tube and may be made of silicone rubber or ChronePrene™. The distal portion houses towards its distal end 4 at least a part of an optical force sensing assembly 20, which is shown in more detail in FIG. 2-6. The force sensing assembly 20 comprises a light source 30 mounted on a light source mounting 53 of a mounting assembly 50 and an optical sensor 40 mounted on an optical sensor mounting 54 of the mounting assembly 50. The mounting assembly 50 further comprising an elastic element 51, which is formed as a helical spring that has a metal core 57 and an outer rim 58, which is formed by an isolating plastic tube. By means of the elastic element 51, the optical sensor mounting 54 and the light source mounting 53 are moveably connected with each other, whereby this connection need not be a fixed connection. Radially outwardly to the elastic element 51, the optical sensor mounting 54 and the light source mounting 53 are sealingly connected by a flexible tube 56, which may consist out of a silicone material. FIG. 2b shows an alternative embodiment of the elastic element, which is formed in this alternative embodiment as an elastic tube 55, which is e.g. made out of Neoprene or ChronoPrene™. The cylindrical wall of this elastic tube 55 may be perforated with openings 55a, which may have a round, oval, or rhomboid shape, as shown in FIG. 2b. The light source mounting 53 and the optical sensor mounting 54 have an outer diameter, which is within tolerance, almost the same as the outer diameter of the electrodes 8, the intermediate isolation elements 28, the flexible tube 56, the tip electrode 6 and the proximal portion 5 of the elongated body 2. The light source mounting 53 and the optical sensor mounting 54 may also function as isolation elements, electrically isolating the tip electrode 6 from the next electrode 8 and also from the optical sensor 40 and the light source 30.

The light source 30 comprises an LED 31 that is mounted on a circuit board 34. The LED 31 functions as a point light source, but it has to be mentioned that other point light sources may be used as well. The LED 31 has a size of e.g. 0.25 mm (width or diameter) in this embodiment, but generally it may have a size smaller than 1 mm. The LED body may have a size of around 1×0.5×0.4 mm or smaller. The light source 30 cooperates with a diffusor 32, which is mounted on the light source 30, coaxially to an optical light source axis A, which is defined by the light source 30, especially by the LED 31.

The optical sensor 40 defines an optical sensor axis B, which is in the initial state of the elongated medical device 1 coaxially with the optical light source axis A. The optical sensor 40 is formed as a camera module, especially as a wafer-level camera, and comprises a pixel array 41 with a number of n pixels 42 (see FIG. 7 to 12) that are arranged on a circuit board 45. Wafer-level camera also comprises an optical element 44, like a lens, that is coaxially with the optical sensor axis B. Wafer-level camera (camera module or optical sensor 40) has a view angle ω in air between 60 and 180 degrees, especially between 90 and 120 degrees. Optical sensor 40 further comprises a housing 46 that houses on the one end the circuit board 45 with the pixel array 41 and on its other end along the optical sensor axis B the optic element 44. In this embodiment, the optic element 44 is a lens with F 6.0 and 90 degree wide angle. The optical sensor 40 is connected via a line 12 with a data processing and control unit 15 (see FIG. 1), which energizes and controls the optical sensor 40 and which also processes sensor data received from the optical sensor 40 and outputs these force sensor data via a data output unit 16. Data processing and control unit 15 is also connected with the electrodes 8 and 6 via a line 10 through which it controls and energizes the electrodes 8 and 6. Via line 10, the data processing and control unit 15 is also connected to the light source 30, which is controlled and energized by the data processing and control unit 15 as well. Line 10 is electrically connected to the electrodes 8 and the tip electrode 6 by means of contact points 9. Line 10 and line 12 may be combined in a single ribbon cable, flat conductor, flat flexible cable or the like.

While the tip electrode 6 is used for electro ablation of circular excitation patterns (rotors, e.g. in the left atrium of the heart), the electrodes 8 are used for mapping and localization purposes of the catheter/the elongated medical device 1.

The elongated medical device 1 further comprises a fluid supply line 13, which may be connected to a fluid supply 17 (see FIG. 1). This fluid supply line 13 is hydraulically connected to a hollow spring element 14, which is located radially inwardly of the elastic element 51 and which is hydraulically connected at its second end to a distal fluid supply line 19. Distal fluid supply line 19 is connected to at least one fluid opening 18, through which an irrigation fluid, like e.g. a saline fluid, may flow to the outside of the distal portion 3 of the elongated medical device 1 to irrigate a surrounding portion of the vessel, organ or other body cavity into which the elongated medical device 1 has been introduced. Fluid flow 63 through the fluid supply line 13, the hollow spring element 14, the distal fluid supply line 19 and through the fluid opening 18 to the outside of the elongated medical device 1 is indicated by arrows 63 in FIG. 2.

Preferably, the parts in the area of the optical sensor 40 and the light source 30 are made of or covered with black color to absorb any light which is not directly directed from the light source 30 to the optical sensor 40.

During operation of the elongated medical device 1 in a vessel, organ or other body cavity, the distal end 4, respectively the tip electrode 6 at the distal portion 3, may experience a force F (see FIGS. 3 and 4) in any of the directions X, Y, Z of a Cartesian coordinate system or any combination thereof when contacting an inner wall of a vessel, an organ or other body cavity. Force F may especially be exerted on the distal end 4, when the tip electrode is pressed against the wall at a vessel, an organ or other body cavity to be treated by an ablation procedure, e.g. an electroablation procedure.

In the initial state of the elongated medical device 1 and the optical force sensing assembly 20 when there is no force applied on the distal end 4 of the elongated body 2, the light originating from the light source 30 and the LED 31 is falling into the wafer-level camera (optical sensor 40) and covers an illuminated contiguous array of pixels 43 as can be seen in FIG. 7. A center C of this illuminated contiguous array of pixels 43 is coaxially with the optical sensor axis B and coaxially with the optical light source axis A (see FIGS. 5, 6 and 7).

In the present embodiment, the size of the illuminated contiguous array of pixels 43 in the state of the elongated medical device 1, when there is no force applied to the distal end of the elongated body 2 will be about a $\frac{1}{10}$ of the total number of pixels. I.e. for a pixel array 41 of the size of 65,000 pixels an illuminated contiguous array of pixels 43 of 6,250 pixels. In other embodiments, the size of the illuminated contiguous array of pixels 43 may be somewhere between $\frac{1}{3}$ and $\frac{1}{30}$ of the total number of pixels of the pixel array 41.

As mentioned earlier, an information about the size of the illuminated contiguous array of pixels 43 will be communicated via data line 12 from the wafer-level camera (optical sensor 40) to the data processing and control unit 15, which will indicate force data measured to a user via the data output unit 16.

Figure 3:
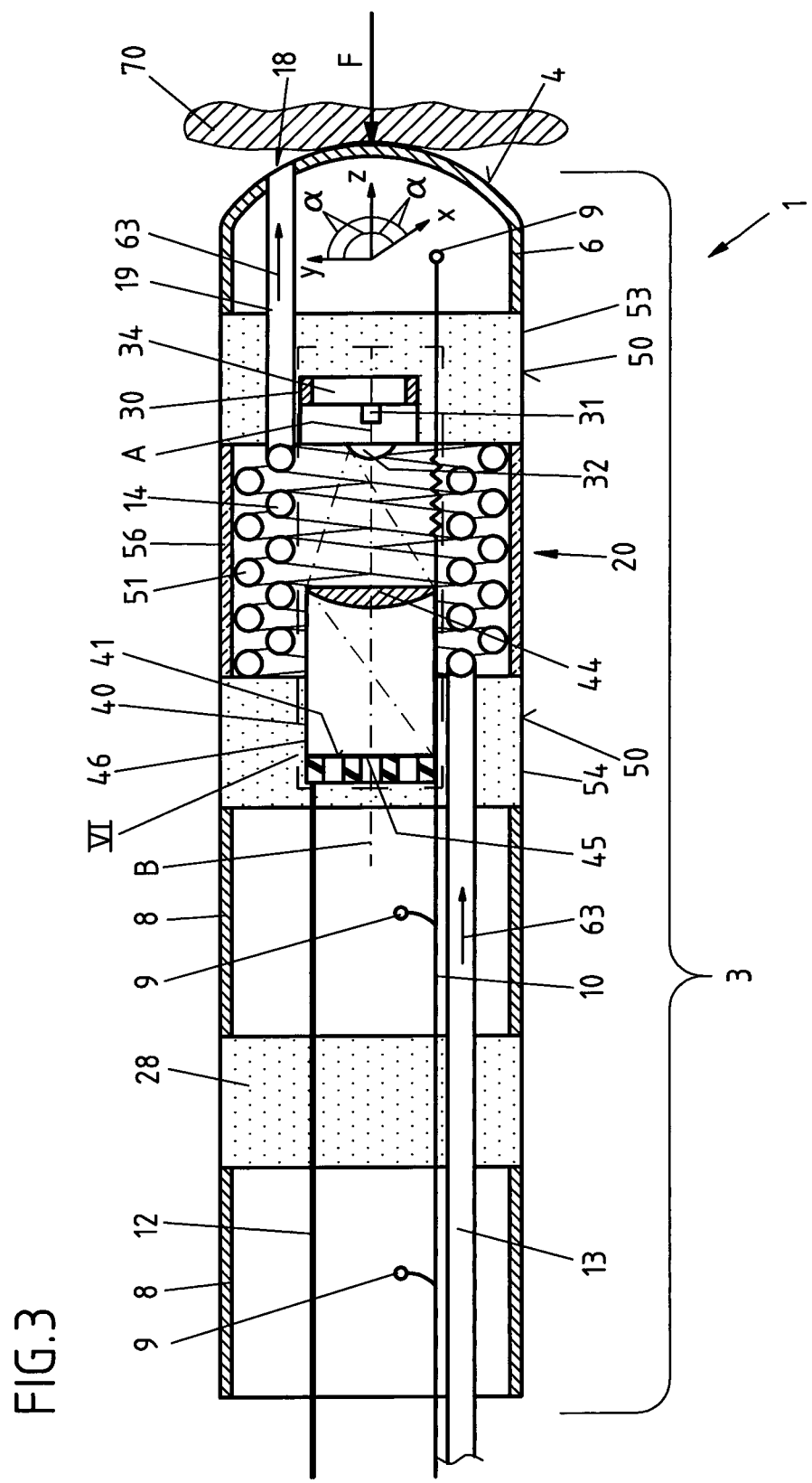
FIG. 3 is a cut view of the distal portion of the elongated medical device corresponding to FIG. 2 in a second state of the medical device with a force applied in direction Z on the distal end of the distal portion.
Figure 6:
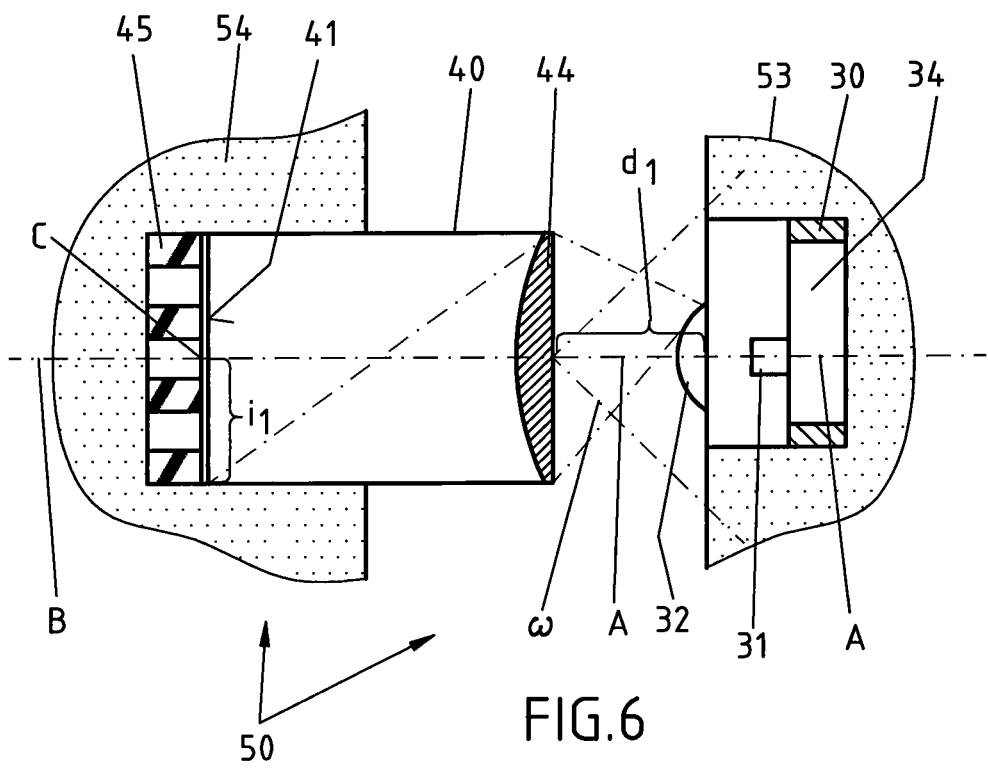
FIG. 6 is an enlarged view according to the marking VI in FIG. 3.

In FIGS. 3, 6 and 8, another state of the elongated medical device 1 is shown where a force F is applied in direction Z, respectively in direction of the optical sensor axis B and the optical light source axis A on the distal end 4 of the distal portion 3. The force F applied in this example is 1 N. Such force may be applied to the distal end 4 of the elongated medical device 1 when the distal end contacts a wall 70 of a vessel, organ or other body cavity to be treated or explored as indicated in FIG. 3. Due to the force F applied to the distal end 4, the optical force sensing assembly 20 is compressed and the axial distance between the light source 30 and the optical sensor 40 is reduced to a distance $d_1$ as is indicated in FIG. 6. The helical spring (elastic element 51) as well as the flexible tube 56 are compressed between the light source mounting 53 and the optical sensor mounting 54. Also, the hollow spring element 14 is compressed in a similar amount. Switching now to FIGS. 6 and 8, the optical sensor 40 now detects an illuminated contiguous array of pixels 43, which is enlarged in its size, characterized by its radius $i_1$ compared to the size of the illuminated contiguous array of pixels 43 (radius $i_0$) in the initial state of the elongated medical device 1 when there was no force applied to the distal end of the elongated medical device 1. See FIGS. 5 and 7 for comparison. While the distance between the optical sensor 30, respectively its optic element 44 and the surface of the light source 30, have been reduced from an initial distance $d_0$ in FIG. 5 to a distance $d_1$ in FIG. 6, whereby $d_1$ is only half of the size of $d_0$, the size of the illuminated contiguous array of pixels 43 has been enlarged from its initial size, characterized by the radius $i_0$ (see FIGS. 5 and 7) of the illuminated contiguous array of pixels 43 to a radius $i_1$ (see FIGS. 6 and 8), which is double the size of the initial radius $i_0$ (for a force of 1 N). As there is no force in a direction X or Y applied to the distal end 4 of the elongated medical device 1, the center C of the illuminated contiguous array of pixels 43 is still coaxial with the optical sensor axis B and the optical light source axis A, as can be seen especially in FIG. 6. The optical sensor data that are delivered from the optical sensor 40 to the data processing and control unit 15 are image data that describe the size of the illuminated contiguous array of pixels 43. In the data processing and control unit 15, these data are processed by an algorithm, which calculates the force F applied to the distal end in the Z direction by means of a formula, which is force (F)=k×$d_0$×(1−$i_0$/$i_1$), whereby k is the spring constant in N/mm, $d_0$ is the distance in mm of the optical sensor 40 to the light source 30 in the initial position of the light source 30 in respect to the optical sensor 40 when no force is applied to the distal end 4 of the elongated body 2, $i_0$ is a measure of the size/radius of the illuminated contiguous pixel array 43 that is receiving light from the light source 30 in the initial position of the light source 30 in respect to the optical sensor 40 when no force is applied to the distal end 4 of the elongated body 2 (see FIGS. 5 and 7) and $i_1$ is a measure of the size/radius of the illuminated contiguous pixel array 43 that is receiving light from the light source 30 in the position of the light source 30 in respect to the optical sensor 40 when the force F is applied to the distal end 4 of the elongated body 2 (see FIGS. 6 and 8). After calculation of the force F, the force F will be output on the data output unit 16 to be recognized by the operator. In the present example, the spring constant k of the elastic element 51 (helical spring) is e.g. 4 N/mm, $d_0$ equals e.g. 0.5 mm and e.g. $i_0/i_1=0.5$. In the data processing and control unit 16, the force F will be calculated based on this formula, and the result of 1 N will be presented on the data output unit 16. If the measured ratio of $i_0/i_1$ is e.g. 0.75188 and $d_0$ is e.g. 0.5 mm and k is e.g. 4 N/mm then the force applied to the tip is 0.5 N. If, for example, the ratio of $i_0/i_1$ is e.g. 0.95 and $d_0$ is e.g. 0.5 mm and k is e.g. 4 N/mm then the force F is 0.1 N, just to give some examples.

Figure 4:
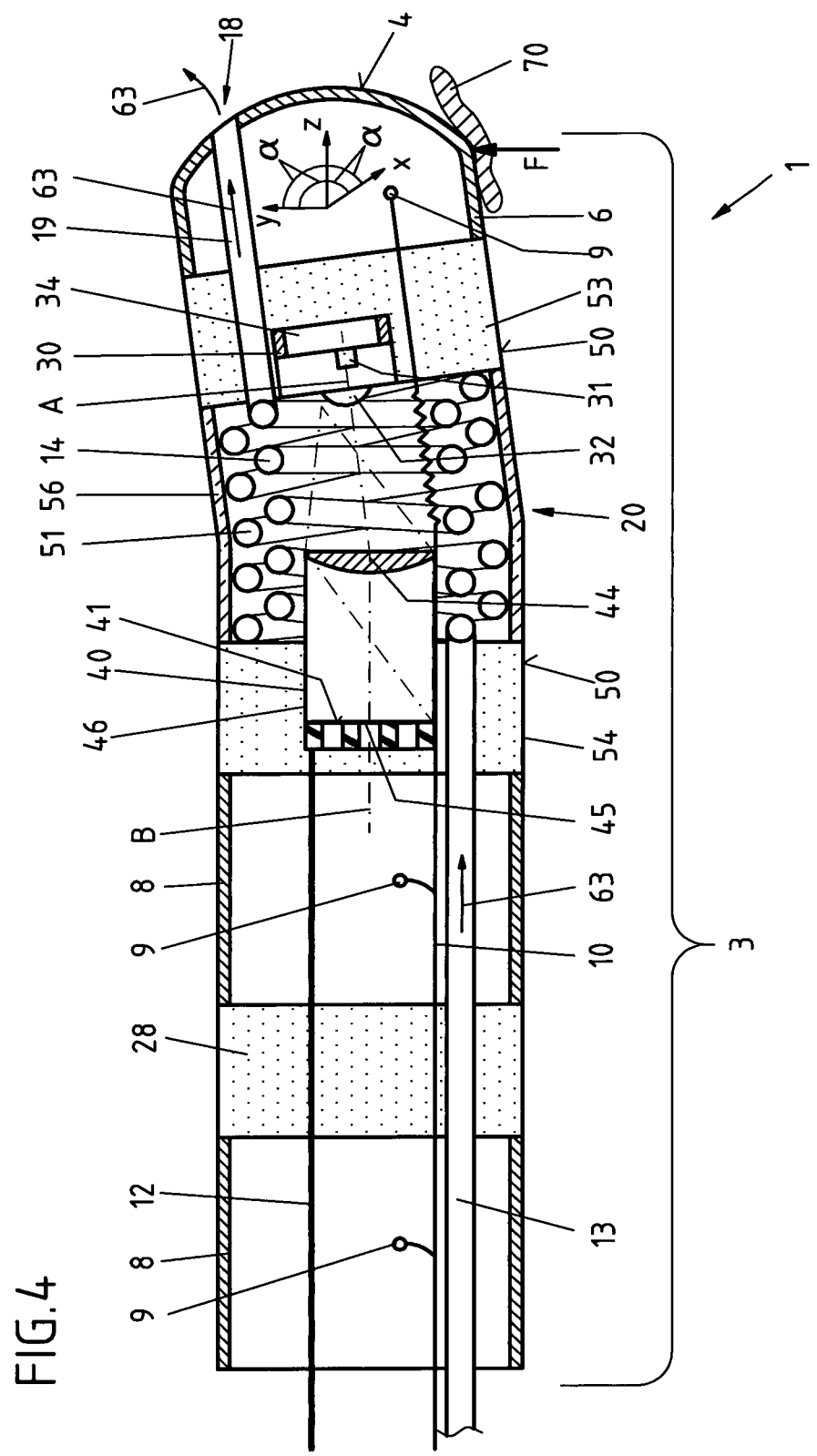
FIG. 4 is a cut view of the distal portion of the elongated medical device corresponding to FIGS. 2 and 3 in a third state of the distal portion with a force applied on a side of the distal end of the distal portion.
Figure 5:
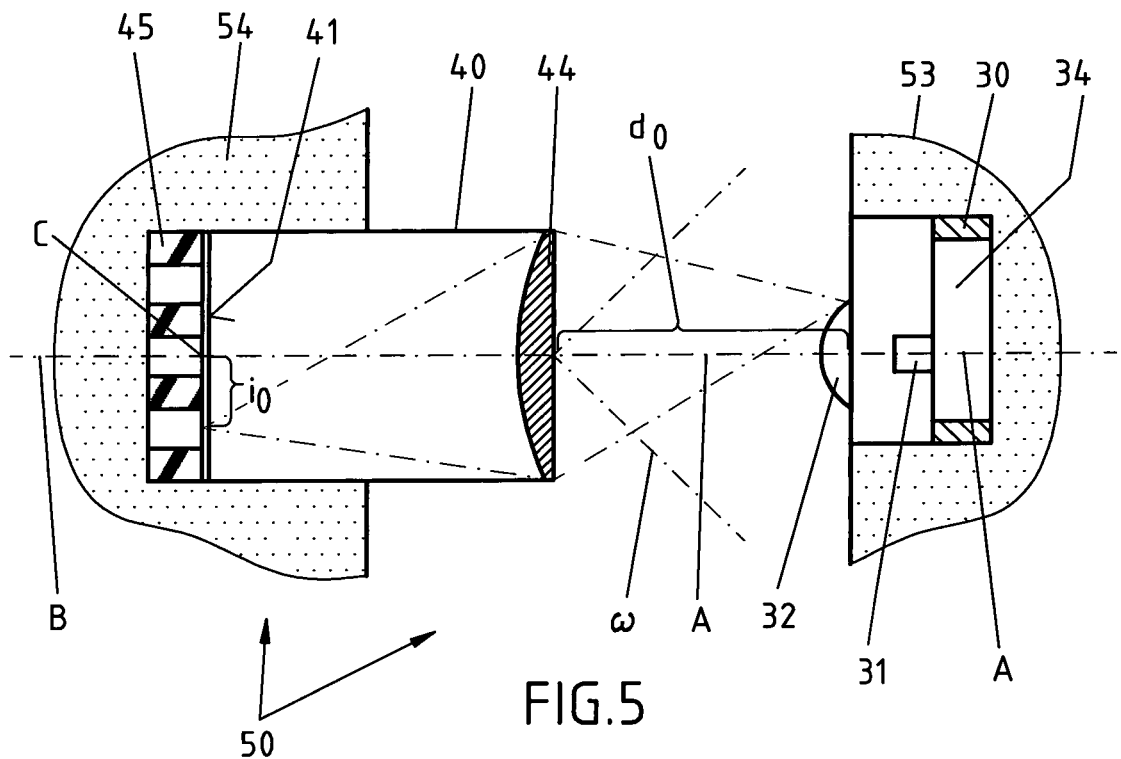
FIG. 5 is an enlarged detail according to the marking V in FIG. 2.

In FIGS. 4 and 12, the elongated medical device 1 and the optical force sensing assembly 20 is displayed in a further state, where a force F is applied to a side of the distal end 4 of the distal portion 3 due to a contact with an inside wall 70 of a vessel, organ or other body cavity as can be seen in FIG. 4. Force F in FIG. 4 is applied in direction Y and results in a distortion of the distal portion 3 of the elongated body including a distortion of the helical spring (elastic element 51) of the mounting assembly 50 and of the hollow spring element 14. This distortion results in a shifting of the illuminated contiguous array of pixels 43 with its center C away from the optical center of the pixel array 41 indicated by the optical axis B as shown in FIG. 12. The optical axis B and the center C of the illuminated contiguous array of pixels 43 are non-coaxial and lie in a distance to each other, indicating the sidewards distortion of the distal end 4/distal portion 3 of the elongated body 2.

Measurement data from the optical sensor 40 will again be communicated via line 12 to the data processing and control unit 16, which will calculate the force F that is exerted on the distal end 4 of the elongated body 2. Force data will then be displayed/outputted by the data output unit 16 for the attention of an operator of the elongated medical device 1.

In FIG. 11 the effect of a sideward distortion of the distal end 4 of the elongated body 2 in the direction opposite to the direction of FIG. 12 is displayed. The illuminated contiguous array of pixels 43 and its center C will move away from the optical axis B in the direction opposite to the one displayed in FIG. 12.

In FIGS. 9 and 10 the effect of forces applied to the distal end 4 of the elongated body 2 in directions perpendicular to the ones displayed in FIGS. 11 and 12 and to the ones shown in FIG. 8 are shown. Of course, any combination of sideward distortions and/or axially exerted forces in that direction may occur and being sensed by the optical force sensing assembly 20.

Figure 13:
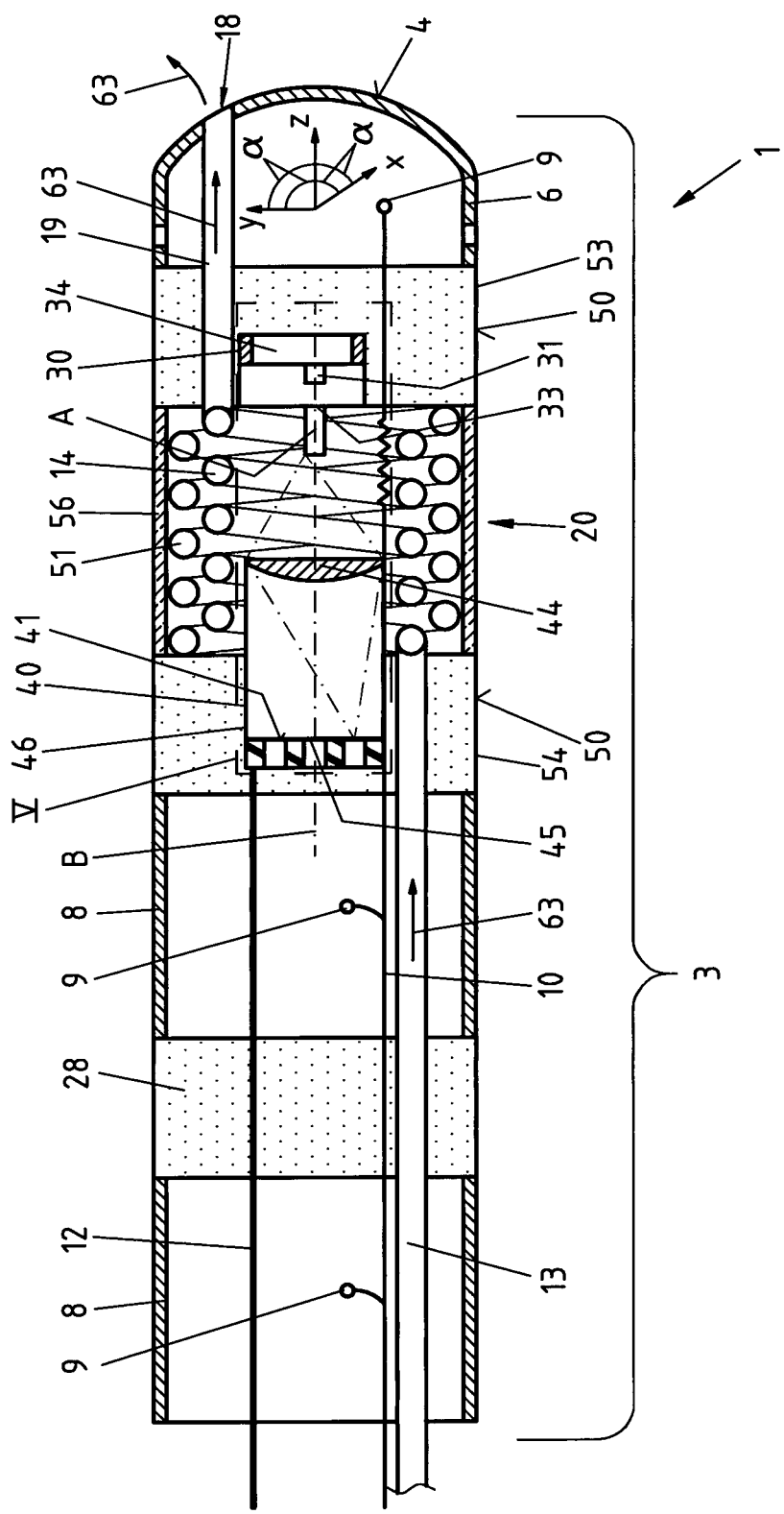
FIG. 13 is a cut view of another embodiment of an elongated medical device, which is formed as a catheter for exploration or treatment of a vessel, organ or other body cavity in the initial state of the medical device when no force is applied to the distal portion.

In FIG. 13 a further embodiment of the elongated medical device 1 is shown. For reference numerals not described in the following text, reference is made to the description of FIGS. 1 to 12 which is herewith incorporated by reference.

The embodiment of FIG. 13 differs from the one described in FIGS. 1 to 12 in that the light source 30 does not cooperate with a diffusor element 32 but does cooperate with a light guide 33 which is attached to the surface of the light source 30 and which is in a coaxial orientation with the optical light source axis A. In case a force is applied to the distal end 4 of the elongated body 2 the optical force sensing assembly 20 will behave in a similar way as described for FIGS. 1 to 12. The description for these figures in this respect is herewith incorporated by reference also for the embodiment of FIG. 13.

Figure 14:
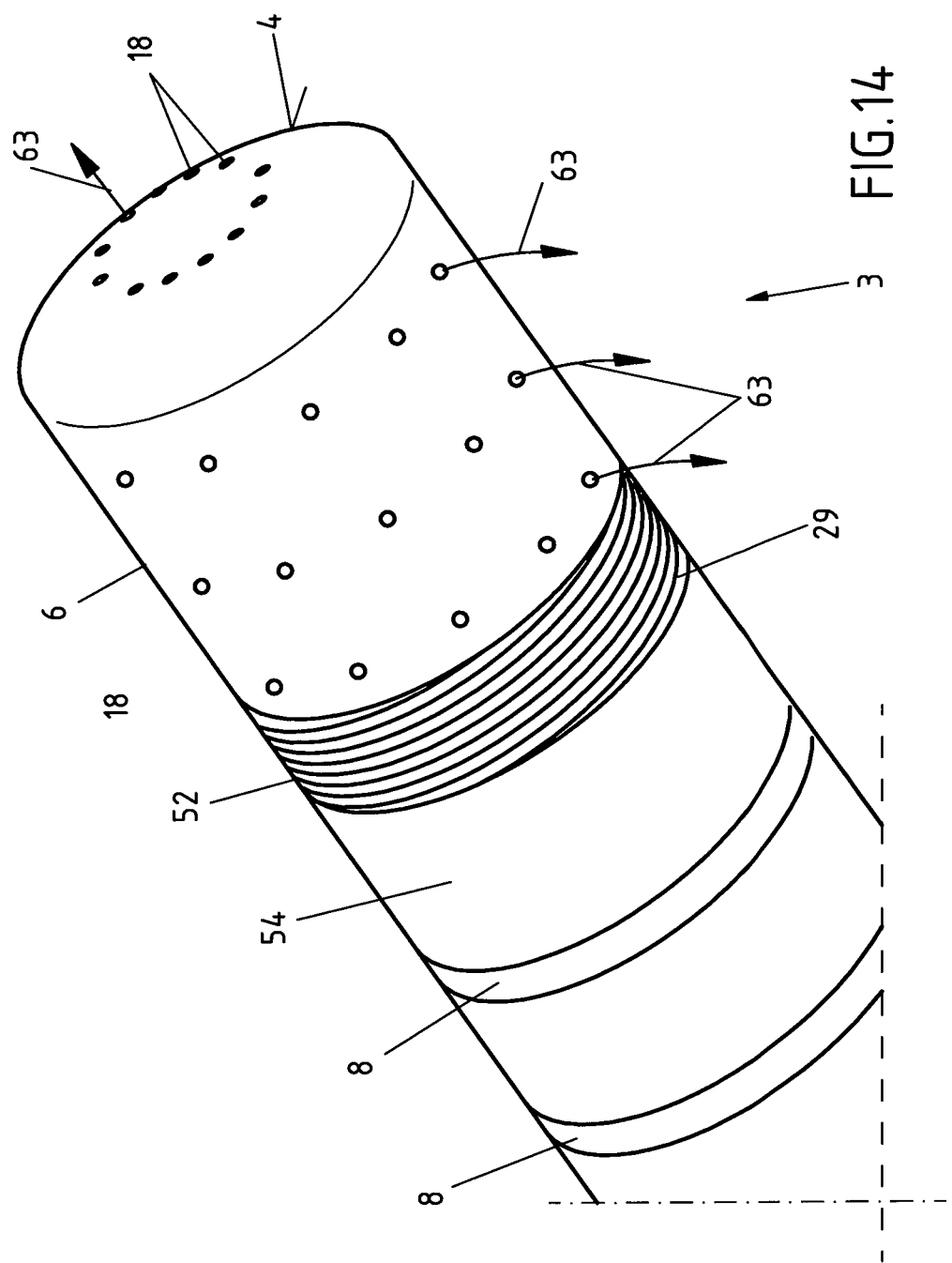
FIG. 14 is a perspective view of the distal portion of a further embodiment of an elongated medical device, which is formed as a catheter for exploration or treatment of a vessel, organ or other cavity in the initial state of the medical device when no force is applied to the distal portion.
Figure 15:
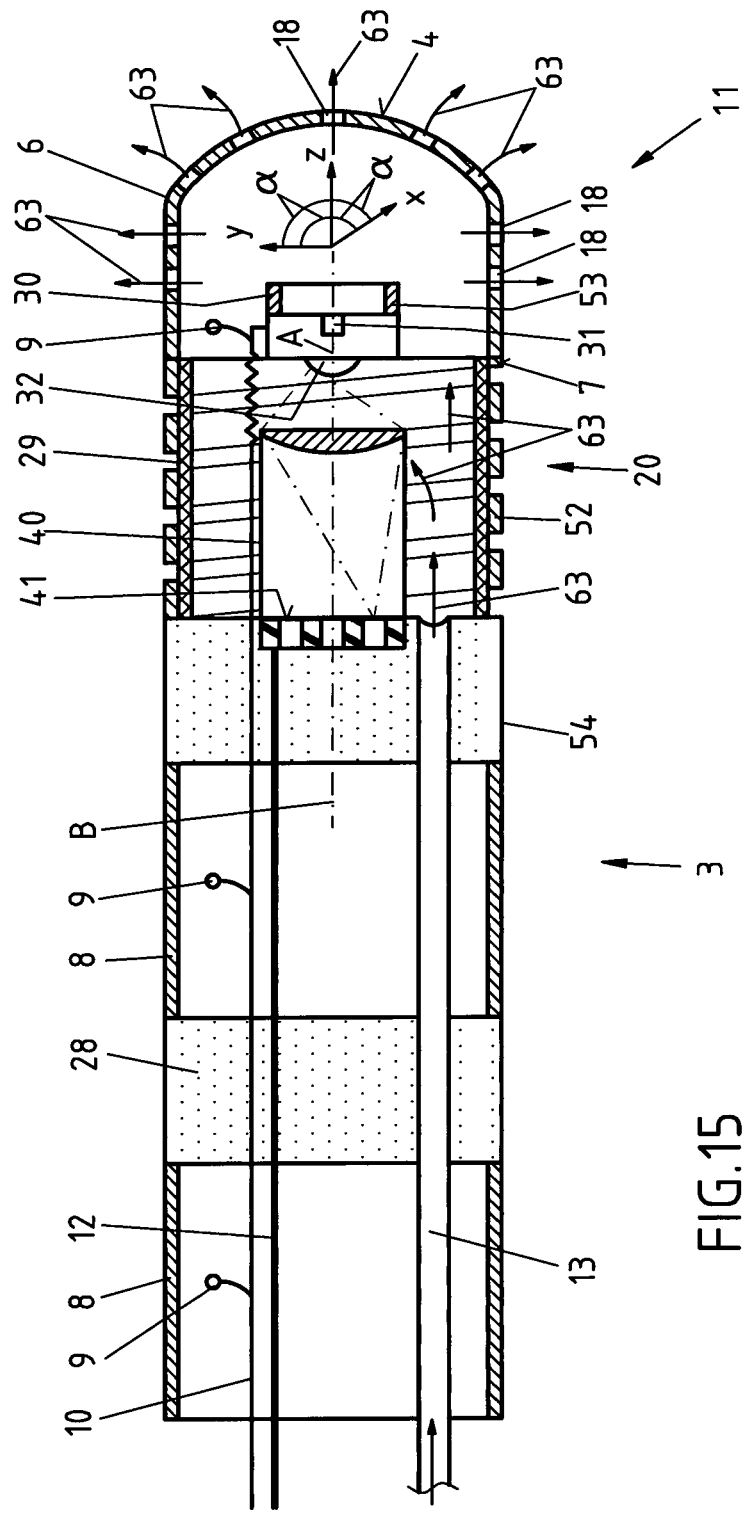
FIG. 15 is a cut view of the distal portion of the elongated medical device corresponding to FIG. 14 in the initial state of the medical device when no force is applied to the distal portion.

In FIGS. 14 and 15 a further embodiment of the elongated medical device 1 is shown. The difference between this embodiment and the embodiments described before is that the elastic element 52 is formed by the sidewall 7 of the tip electrode 6, which means that the elastic element 52 and the tip electrode 6 are formed in one single piece. In the embodiment shown in FIG. 15 the light source cooperates with a diffusor 32. In an alternative embodiment of the embodiment shown in FIG. 15 the light source may again cooperate with a light guide 33 as displayed in FIG. 13.

Instead of an outer flexible tube, the helical spring/elastic element 52 cooperates with a tube 29 which may be formed out of a rubber material, e.g. made of neoprene. This tube is arranged radially inwardly of the elastic element 52 and is sealingly connected to the optical sensor mounting 54. The tube 29 is glued on the inner side of the elastic element 52 and follows every move of this elastic element 52. As can especially be taken out of FIG. 15 the fluid supply line 13 opens into a chamber 27 defined by this tube 29 and the tip electrode 6. The tip electrode 6 in this embodiment has a pattern of fluid openings 18 distributed on the sidewall and its distal end. These fluid openings 18 communicate with this chamber 27 defined by tube 29 and when an irrigation fluid is transported through fluid supply line 13 into the chamber 27, water will flow through the fluid openings 18 to the surrounding area.

It has to be mentioned that the light source 30 as well as the optical sensor 40 are fluid tightly sealed so that no irrigation fluid may enter any of these electronic/optic components.

In respect to the function of the optical force sensing assembly 20 and the other parts of the elongated medical device 1 displayed here, it is referred to the description for FIGS. 1 to 13 which is herewith enclosed by reference.

Figure 16:
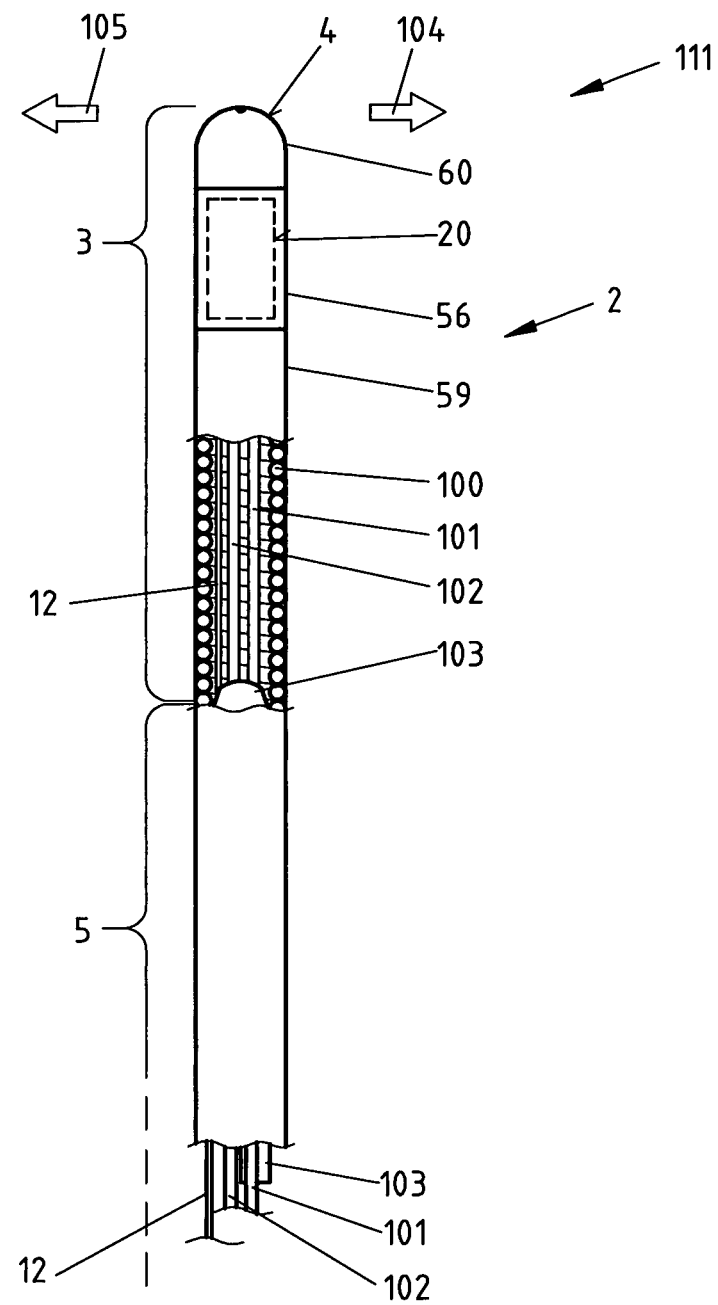
FIG. 16 is a schematic view of an elongated medical device in a further embodiment, which is a guide wire for guiding a catheter through a vessel, organ or other body cavity.

In FIG. 16, a further embodiment of an elongated medical device is shown. The elongated medical device 111 is formed as a guide wire, which is e.g. used to guide a catheter, such as an ablation catheter, through a vessel, organ or other body cavity. The elongated medical device 111 comprises an elongated body 2, which is only partly shown in FIG. 16. At a distal portion of the elongated medical device 111, an optical force sensing assembly 20 is arranged close to the distal end 4 of the distal portion 3. The optical force sensing assembly 20 is similar to the one shown and described e.g. in FIGS. 5 and 6 as well as in FIG. 2 to 4 or the one shown and described in FIG. 13 or 15. The respective description of the optical force sensing assembly 20 of the embodiments shown in FIGS. 2 to 6, 13 and 15 is enclosed herewith by reference. The part of the elongated medical device 111, which includes the optical sensor mounting, comprises a flexible tube 56, which is e.g. made out of a flexible silicone and which is arranged radially outwardly of the optical force sensing assembly 20. The flexible tube 56 seals the area of the optical force sensing assembly 20 against any fluids such as e.g. blood.

The distal end 4 of the elongated medical device 111 has a tip 60, which may be made out of metal, e.g. stainless steel, platinum, iridium, titanium or nitinol, and which is sealingly connected to the tube 56. Tip 60 is attached to the optical force sensing assembly 20 in a way that any force applied to the tip 60 will be sensed by the optical force sensing assembly 20. In the area adjacent to the optical force sensing assembly 20 in direction of the main body 5 of the elongated medical device 111, there is arranged a portion which includes a helical spring element 100 which is radially outwardly surrounded by a flexible tube 59, which may again be e.g. made out of an elastic silicone material. Inside of this helical spring element 100, there is arranged a first wire element 101 and a second wire element 102, which are both used to steer the elongated medical device 111 in a way that if e.g. wire element 101 is pulled in direction away from the distal end 4, the distal portion 3 of the elongated medical device 111 will bend in a direction 104 while if the second wire element 102 is pulled in a direction away from the distal end 4, the distal portion 3 of the elongated medical device 111 will bend in a direction 105, which is opposite to direction 104. Hence, through the wire elements 101 and 102, the elongated medical device 111 may be steered through vessels, organs or other body cavities. As the body of the elongated medical device 111 may also be rotated, the elongated medical device 111 may be directed/steered into any direction.

Further, a supply and data line 12 is guided through the helical spring element 100 as well as through the proximal portion 5 of the elongated medical device 111 and may be connected to a control and supply unit 15 as well as to an output unit 16, which have been shown in FIG. 1. Within the proximal portion 5 of the elongated medical device, there is arranged a guide tube 103 through which the wire elements 101 and 102 are guided.

In respect to the function of the optical force sensing assembly 20 and the other parts of the elongated medical device 111 displayed here, it is referred to the description for FIG. 1 to 15, which is enclosed herewith by reference.

REFERENCE LIST 1 elongated medical device
2 elongated body
3 distal portion
4 distal end
5 proximal portion
6 tip electrode
7 sidewall (of 6)
8 electrodes
9 contact points
10 line
11 further elongated medical device
12 data line
13 fluid supply line
14 hollow spring element
15 data processing and control unit
16 data output unit
17 fluid supply
18 fluid opening
19 distal fluid supply line
20 optical force sensing assembly
27 chamber
28 intermediate (isolation) elements
29 tube
30 light source
31 LED
32 diffusor
33 light guide
34 circuit board
40 optical sensor
41 pixel array
42 pixels
43 illuminated contiguous array of pixels
44 optic element
45 circuit board
46 housing
50 mounting assembly
51 elastic element (helical spring)
52 further elastic element (spiraled side wall)
53 light source mounting
54 optical sensor mounting
55 elastic element (elastic tube)
55b openings
56 flexible tube
57 core
58 rim
60 tip
63 direction of fluid flow
70 wall
100 guide spring element
101 first wire element
102 second wire element
103 guide tunnel
104 direction
105 direction
111 elongated medical device (guide wire)
ω view angle of 40
α a right angle (between Z and X, Z and Y, X and Y)
A optical light source axis
B optical sensor axis
C center (of 43)
$d_0$, $d_1$ distance
F Force
$i_0$, $i_1$ radius of 43
X direction
Y direction
Z direction

The invention claimed is:

1. A medical optical force sensing assembly configured for use in a distal portion of an intravascular catheter, comprising:
   a light source configured to define a linear optical light source axis (A);
   an optical sensor configured to define a linear optical sensor axis (B) and to face the light source, the optical sensor being arranged at a distance ($d_0$, $d_1$) from the light source along the optical axis (B);
   a mounting assembly for the optical sensor and the light source comprising a compressible elastic element configured to permit relative movement between the light source and the optical sensor at least in directions X, Y, Z of a Cartesian coordinate system, wherein the direction Z is parallel to the optical light source axis and to the optical sensor axis (B) at least when the distal portion of the intravascular catheter is in an initial undeformed state and not subjected to a force (F) operating thereon, and wherein the X and Y directions are perpendicular to one another and are also perpendicular to the Z direction;
   and further wherein the optical sensor comprises a camera module having an array of n pixels, where the n pixels are configured to receive light from the light source, and where a size of the pixel array illuminated by the light source is proportional to the force (F) as the force (F) is applied in the Z direction to the compressible elastic member through the distal portion of the intravascular catheter.

2. The medical optical force sensing assembly according to claim 1, wherein a deviation in a shape of the illuminated pixel array provides a measure of the force (F) as the force (F) is applied in one or more of the X and Y directions.

3. The medical optical force sensing assembly according to claim 1, wherein the camera module comprises a wafer-level camera.

4. The medical optical force sensing assembly according to claim 1, wherein the camera module has a view angle (α) in air between 60 and 180 degrees, or between 90 and 120 degrees.

5. The medical optical force sensing assembly according to claim 1, wherein the distance ($d_0$) has a maximum length of 10 mm, 1 mm, or 0.5 mm.

6. The medical optical force sensing assembly according to claim 1, wherein the camera module is at least one of smaller than 1.5 mm×1.5 mm in width, and smaller than 1.5 mm in diameter, where each of the width and diameter is in a direction perpendicular to the optical sensor axis (B).

7. The medical optical force sensing assembly according to claim 1, wherein the light source is a point light source or an LED.

8. The medical optical rce sensing assembly according to claim 7, wherein the light source comprises at least one of a light guiding fiber, a light guide, and a diffusor.

9. The medical optical force sensing assembly according to claim 1, wherein the pixel array comprises a contiguous array of pixels.

10. The medical optical force sensing assembly according to claim 1, wherein the compressible elastic element comprises at least one of a helical spring, an elastic tube, and a rubber-like material.

11. The medical optical force sensing assembly according to claim 1, wherein the compressible elastic element comprises at least partially a rubber-like material.

12. The medical optical force sensing assembly according to claim 1, wherein the mounting assembly is incorporated into the distal portion of the intravascular catheter.

13. The medical optical force sensing assembly according to claim 1, wherein the force (F), applied in the Z direction, is calculated by a formula $F=k*d_0*(1-i_0/i_1)$, wherein k is a spring constant in N/mm, do is the distance (d) in mm of the optical sensor to the light source in the initial undeformed state of the distal portion of the intravascular catheter when the distal portion is not subjected to the force (F) operating thereon, $i_0$ is a measure of the size of the illuminated pixel array in the initial undeformed state of the distal portion of the intravascular catheter when the distal portion is not subjected to the force (F) operating thereon, and $i_1$ is a measure of the size of the illuminated pixel array in a position of the light source in respect of the optical sensor when the force (F) is applied to the compressible elastic member through the distal portion of the intravascular catheter.

14. The medical optical force sensing assembly according to claim 1, wherein, in operation, a center (C) of the illuminated pixel array is coaxial with the optical sensor axis (B) when the force (F) is not applied to the distal portion of the intravascular catheter in the X or Y directions and further wherein, in operation, the center (C) of the illuminated pixel array is non-coaxial to the optical sensor axis (B) when the force (F) is applied to the distal portion of the intravascular catheter in one or more of the X or Y directions.

15. The medical optical force sensing assembly according to claim 1, wherein the optical force sensing assembly is configured to be connected to a data processing and control unit configured to process force sensing data delivered from the optical sensor via a data line and to provide output force data by means of a data output unit.

16. The medical optical force sensing assembly according to claim 1, wherein the assembly is included in the intravascular catheter, the catheter being configured to explore or treat a vessel, organ or body cavity.

17. The medical optical force sensing assembly according to claim 16, wherein the intravascular catheter further comprises a guide wire configured to guide the catheter through the vessel, organ or body cavity.

* * * * *